United States Patent [19]
Erickson et al.

[11] Patent Number: 6,090,827
[45] Date of Patent: Jul. 18, 2000

[54] PHARMACEUTICAL FORMULATION OF OMEPRAZOLE

[75] Inventors: Magnus Erickson; Lars Josefsson, both of Mölndal, Sweden

[73] Assignee: AstraZeneca AB, Sodertalje, Sweden

[21] Appl. No.: 09/077,717

[22] PCT Filed: May 18, 1998

[86] PCT No.: PCT/SE98/00922

§ 371 Date: Jun. 8, 1998

§ 102(e) Date: Jun. 8, 1998

[87] PCT Pub. No.: WO98/53803

PCT Pub. Date: Dec. 3, 1998

[30] Foreign Application Priority Data

May 28, 1997 [SE] Sweden .................................. 970200

[51] Int. Cl.⁷ .................................................. A61K 31/44
[52] U.S. Cl. ............................................................ 514/338
[58] Field of Search ............................................. 514/338

[56] References Cited

U.S. PATENT DOCUMENTS

| | | | |
|---|---|---|---|
| 4,786,505 | 11/1988 | Lovgren et al. | 424/468 |
| 5,372,998 | 12/1994 | Kokubo et al. | 514/57 |

FOREIGN PATENT DOCUMENTS

| | | |
|---|---|---|
| 0005129 | 10/1979 | European Pat. Off. . |
| 0124495 | 11/1984 | European Pat. Off. . |
| 0247983 | 12/1987 | European Pat. Off. . |
| 9427988 | 12/1994 | WIPO . |
| 9501977 | 1/1995 | WIPO . |
| 9601623 | 1/1996 | WIPO . |

OTHER PUBLICATIONS

Pilbrant, A. et al., "Development of an oral formulation of omeprazole", *Scand. J. Gastroenterol,* 1985; 20 (suppl): 113–120.

*Primary Examiner*—Raymond Henley, III
*Attorney, Agent, or Firm*—White & Case LLP

[57] ABSTRACT

An enteric coated oral pharmaceutical formulation comprising as active ingredient a compound selected from the group of omeprazole, an alkaline salt of omeprazole, the (−)-enantiomer of omeprazole and an alkaline salt of the (−)-enantiomer of omeprazole, wherein the formulation comprises a core material of the active ingredient and optionally an alkaline reacting compound, the active ingredient is in admixture with a pharmaceutically acceptable excipient, such as for instance a binding agent, and on said core material a separating layer and an enteric coating layer. A hydroxypropyl methylcellulose (HPMC) of low viscosity with a specific cloud point is used in the manufacture of pharmaceutical formulations. Furthermore, the application describes the processes for their preparation and the use of the claimed formualtions in medicine.

21 Claims, 2 Drawing Sheets

PHARMACEUTICAL FORMULATION OF OMEPRAZOLE

This is a 371 of PCT/SE98/00922 filed May 18, 1998.

FIELD OF THE INVENTION

The present invention relates to an oral pharmaceutical formulation comprising the acid labile $H^+$, $K^+$-ATPase inhibitor omeprazole. The formulation is in the form of a multiple unit dosage form comprising enteric coating layered units of omeprazole. More specifically, the units comprise a core material of omeprazole and optionally an alkaline reacting substance, in admixture with one or more pharmaceutically acceptable excipients such as a binding, filling and/or disintegrating agent. Furthermore, each unit comprises a separating layer to separate the enteric coating layer from the core material. The separating layer and/or the optional binding agent consists of a specific quality of hydroxypropyl methylcellulose (HPMC), and optionally pharmaceutical excipients. More specifically, the HPMC quality has a specific cloud point.

Furthermore, the present invention refers to the use of a specific quality of HPMC in the manufacture of a pharmaceutical formulation comprising omeprazole, and the use of such a pharmaceutical formulation in medicine.

BACKGROUND OF THE INVENTION

Omeprazole, an alkaline salt thereof, the (−)-enantiomer of omeprazole and an alkaline salt of the (−)-enantiomer of omeprazole, all compounds hereinafter referred to as omeprazole, are used in the treatment of gastric acid related diseases. Omeprazole and pharmaceutically acceptable salts thereof are described in EP 5129, and some specific alkaline salts of omeprazole are described in EP 124 495 and WO95/01977. Certain salts of the single enantiomers of omeprazole and their preparation are described in WO94/27988.

Omeprazole is generally known to be useful for inhibiting gastric acid secretion in mammals and man by controlling gastric acid secretion at the final step of the acid secretory pathway. Thus, in a more general sense, it may be used for prevention and treatment of gastric-acid related diseases in mammals and man, including e.g. reflux oesophagitis, gastritis, duodenitis, gastric ulcers and duodenal ulcers. Furthermore, it may be used for treatment of other gastrointestinal disorders where gastric acid inhibitory effect is desirable e.g. in patients on NSAID therapy, in patients with non ulcer dyspepsia, in patients with symptomatic gastro-oesophageal reflux disease, and in patients with gastrinomas. It may also be used in patients in intensive care situations, in patients with acute upper gastrointestinal bleeding, pre- and postoperatively to prevent aspiration of gastric acid and to prevent and treat stress ulceration. Further, it may be useful in the treatment of psoriasis as well as in the treatment of Helicobacter infections and diseases related to these, as well as in the treatment or prophylaxis of inflammatory conditions in mammals, including man.

Omeprazole is, however, susceptible to degradation or transformation in acidic and neutral media. The degradation is catalyzed by acidic compounds and is stabilized in mixtures with alkaline compounds. The stability of omeprazole is also affected by moisture, heat, organic solvents and to some degree by light.

With respect to the stability properties of omeprazole, it is obvious that an oral solid dosage form must be protected from contact with the acidic gastric juice and that omeprazole must be transferred in intact form to that part of the gastrointestinal tract where pH is near neutral and where rapid absorption can occur.

A pharmaceutical oral dosage form of omeprazole is best protected from contact with acidic gastric juice by an enteric coating layer. In EP 247 983 such an enteric coated formulation of omeprazole is described. The formulation contains omeprazole in the form of a core unit containing omeprazole together with an alkaline salt or containing an alkaline salt of omeprazole optionally together with an alkaline salt, the core unit is layered with a separating layer and an enteric coating layer. In WO 96/01623 a multiple unit tableted dosage formulation of omeprazole is described.

The oral formulations described in EP 247 983 and the tablet formulations decribed in WO 96/01623 are enteric coating layered formulations which comprise or may comprise a separating layer to separate the acidic enteric coating material from omeprazole being an acid susceptible substance. HPMC of low viscosity may be used as a binding agent in the core material or as a layer separating the core material from the enteric coating layer in the described formulations. All ingredients, including HPMC qualities, used in a pharmaceutical preparations must fulfill strict criteria, such as for instance requirements defined in pharmacopoeial monographs.

The rate of release of omeprazole from a pharmaceutical dosage form can influence the total extent of absorption of omeprazole into the general circulation (Pilbrant and Cederberg, Scand. J. Gastroenterology 1985; 20 (suppl. 108) p. 113–120). Therefore the limits for rate of release of the omeprazole from the pharmaceutical formulation are stated in the marketing approval for the products.

It has now surprisingly been found that different batches of low viscosity HPMC, which fulfill all pharmacopoeial requirements, used as binder in the formation of omeprazole containing cores or as material for the separating layer of enteric coating layered formulations of omeprazole, may differ with respect to their ability of influencing the rate of release of omeprazole in simulated intestinal fluid, USP, in vitro. One parameter of interest in the release rate influensing ability of the HPMC is its water solublity.

The aqueous solubility of HPMC decreases with increasing temperature due to polymer phase separation. This is observed as a clouding of the polymer solution when the temperature is increased. Cloud point is the temperature at which this polymer phase separation occurs. Cloud point is determined by measuring the light transmission through the polymer solution. The light transmission of a specific system where the polymer is dissolved, that is a transparent polymer solution without clouding, is defined as light transmission 100%. In this patent application cloud point is defined as the temperature where the light transmission of a specific system is 96% when a commercial instrument from Mettler is used. For other cloud point systems and instruments another light transmission may be specified for each system.

One problem which can be avoided by the new formulation and use of a specific quality of HPMC is that the amount of product discard can be reduced. From an economical aspect it is advantageous to specify and check the HPMC quality and keep the discard of produced pharmaceutical product low.

OUTLINE OF THE INVENTION

It has now been found that a quality of HPMC with a cloud point of not less than 45.6° C. determined as the temperature where the light transmission of a specified system is 96% measured by a Mettler FP90/FP81C instrument is desirable in an enteric coating layered pharmaceutical formulation comprising omeprazole. Alternatively, when another instrument is used for determination, the cloud point may be specified as not less than 44.5° C. when determined as the temperature where the light transmission is 95% measured by a spectrophotometer. The two different apparatuses used in cloud point determination are described more in detail in the experimental section, below. An upper limit for the cloud point is not critical and therefore there is no need to specify that.

The HPMC is used as a binding agent and/or as a constituent of a separating layer separating the core material from the enteric coating layer. The HPMC quality defined in the present patent application is desirable in fulfilling the criteria on rate of release of omeprazole and to be suitable for oral administration of omeprazole.

DETAILED DESCRIPTION OF THE INVENTION

Core Materials

Figure 1:
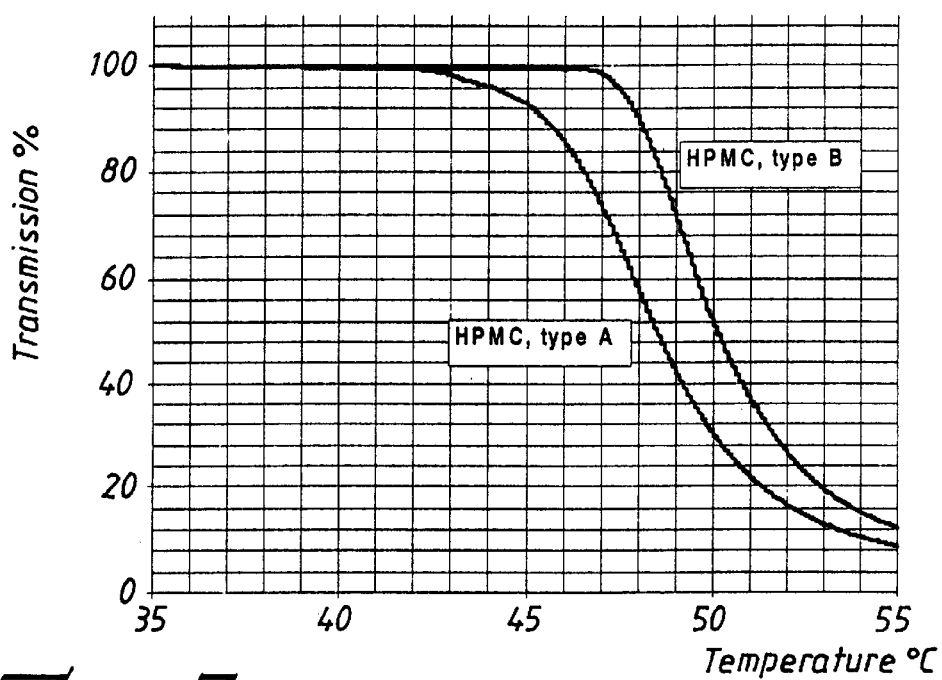
FIG. 1 shows two graphs representing two different batches of low viscosity HPMC named Type A and Type B. The graphs show cloud point determinations for the two HPMC batches used as a constituent of the separating layer described in Example 1 below. With a separating layer comprising HPMC Type A the release of omeprazole was not acceptable for a pharmaceutical product, and with the HPMC Type B none of the discussed problems with the rate of release of omeprazole in an oral formulation occured.

Omeprazole with formula Ia, is preferably formulated into an oral composition in the form of a pharmaceutically acceptable salt, such as an alkaline salt selected from the group of the $Mg^{2+}$, $Ca^{2+}$, $Na^+$ and $K^+$ salts, more preferably the $Mg^{2+}$ salt. Omeprazole may also be used in the form of the (−)-enantiomer of omeprazole or an alkaline salt of the (−)-enantiomer of omeprazole.

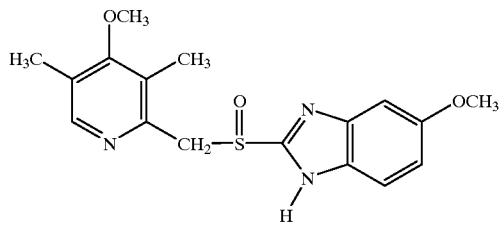

(Ia)

The core material for the individually enteric coating layered pellets can be composed and formulated according to different principles, such as described in EP 247 983 and WO 96/01623 hereby incorporated by reference. For instance, omeprazole is mixed with pharmaceutical constituents to obtain preferred handling and processing properties and a suitable concentration of omeprazole in the final mixture. Pharmaceutical constituents such as fillers, binders, lubricants, disintegrating agents, surfactants and other pharmaceutically acceptable additives, can be used.

Preferably, omeprazole, optionally after mixing with alkaline compounds, is mixed with suitable constituents including a binding agent and formulated into a core material. Said core materials may be produced by extrusion/spheronization, balling or compression utilizing different process equipments. The formulated core materials may have a size of less than approximately 2 mm. The manufactured core materials can be layered further with additional ingredients, optionally comprising active substance, and/or be used for further processing.

Alternatively, inert seeds layered with active substance (the active substance is optionally mixed with alkaline compounds) can be used as the core material for the further processing. The seeds, which are to be layered with the active substance, can be water insoluble seeds comprising different oxides, celluloses, organic polymers and other materials, alone or in mixtures or water soluble seeds comprising different inorganic salts, sugars, non-pareils and other materials, alone or in mixtures.

Before the seeds are layered, for instance by using granulating or spray coating/layering equipment, omeprazole is mixed with a binding agent and optionally further components.

Such further components can be binders, surfactants, fillers, disintegrating agents, alkaline additives or other pharmaceutically acceptable ingredients, alone or in mixtures.

The binders are for example celluloses such as hydroxypropyl methylcellulose, hydroxypropyl cellulose, microcrystalline cellulose and carboxymethyl-cellulose sodium, polyvinyl pyrrolidone, sugars, starches and other pharmaceutically acceptable substances with cohesive properties. If hydroxypropyl methylcellulose is used as the binding agent, it is preferably a quality of HPMC with a cloud point of not less than 45.6° C. determined as the temperature where the light transmission of a specified system is 96% measured by a Mettler FP90/FP81C instrument, or alternatively the HPMC quality has a cloud point of not less than 44.5° C. determined as the temperature where the light transmission is 95% measured by a spectrophotometer. Suitable surfactants are found in the groups of pharmaceutically acceptable non-ionic or ionic surfactants, such as for instance sodium lauryl sulphate.

The active substance may also be mixed with an alkaline pharmaceutically acceptable substance (or substances). Such substances can be chosen among, but are not restricted to, substances such as the sodium, potassium, calcium, magnesium and aluminium salts of phosphoric acid, carbonic acid, citric acid or other suitable weak inorganic or organic acids; aluminium hydroxide/sodium bicarbonate coprecipitate; substances normally used in antacid preparations such as aluminium, calcium and magnesium hydroxides; magnesium oxide or composite substances, such as $Al_2O_3.6MgO.CO_2.12H_2O$, $Mg_6Al_2(OH)_{16}CO_3.4H_2O$, $MgO.Al_2O_3.2SiO_2.nH_2O$ or similarcompounds; organic pH-buffering substances such as trihydroxymethylaminomethane, basic amino acids and their salts or other similar, pharmaceutically acceptable pH-buffering substances.

Alternatively, the aforementioned core material can be prepared by using spray drying or spray congealing technique.

Separating Layer(s)

The core material containing omeprazole must, according to EP 247 983, be separated from the enteric coating polymer(s) containing free carboxyl groups, which may otherwise cause degradation/discolouration of omeprazole during the coating process or during storage.

According to the present invention, the separating layer comprises a specific quality of low viscosity HPMC, especially a HPMC with a viscosity of preferably less than 7.2 cps in 2% aqueous solution. This specific quality of HPMC should preferably have a cloud point of at least 45.6° C. determined by a Mettler instrument. The determination of cloud point may be performed in another instrument and system as described in detail in the experimental section. The cloud point is determined in a mixed disodium hydrogenphosphate buffer 0.235 M and simulated gastric fluid pH 1.2 in the proportions 4:5. The mixed solution used for the cloud point determination has a pH of 6.75–6.85. The concentration of HPMC in the mixed solution is 1.2% (w/w) for the Mettler instrument. For more detailed information on the composition of the mixed solution, see below in the experimental section.

Alternatively, the quality of HPMC is determined by a method which correlates with the above described methods, e.g. NIR spectrophotometry.

Additives such as plasticizers, colorants, pigments, fillers, anti-tacking and anti-static agents, such as for instance magnesium stearate, titanium dioxide, talc and other additives may also be included in the separating layer(s).

Enteric Coating Layer(s)

One or more enteric coating layers are applied onto the core material covered with separating layer(s) by using a suitable coating technique. The enteric coating layer material may be dispersed or dissolved in either water or in a suitable organic solvent. As enteric coating layer polymers one or more, separately or in combination, of the following can be used; e.g. solutions or dispersions of methacrylic acid copolymers, cellulose acetate phthalate, cellulose acetate butyrate, hydroxypropyl methylcellulose phthalate, hydroxypropyl methylcellulose acetate succinate, polyvinyl acetate phthalate, cellulose acetate trimellitate, carboxymethylethylcellulose, shellac or other suitable enteric coating layer polymer(s). For environmental reasons, an aqueous coating process may be preferred. In such aqueous processes methacrylic acid copolymers are most preferred.

The enteric coating layers may contain pharmaceutically acceptable plasticizers to obtain desirable mechanical properties, such as flexibility and hardness of the enteric coating layers. Such plasticizers are for instance, but not restricted to, triacetin, citric acid esters, phthalic acid esters, dibutyl sebacate, cetyl alcohol, polyethylene glycols, polysorbates or other plasticizers. The amount of plasticizer is optimized for each enteric coating layer formula, in relation to selected enteric coating layer polymer(s), selected plasticizer(s) and the applied amount of said polymer(s). Additives such as dispersants, colorants, pigments, polymers e.g. poly(ethylacrylate, methylmethacrylate), anti-tacking and anti-foaming agents may also be included in the enteric coating layer(s). Other compounds may be added to increase film thickness and to decrease diffusion of acidic gastric juices into the acidic susceptible active substance.

To protect the acidic susceptible active substance, the enteric coating layer(s) preferably constitute(s) a thickness of at least approximately 10 $\mu$m. The maximum thickness of the applied enteric coating layer(s) is normally only limited by processing conditions.

The pellets or units covered with enteric coating layer(s) may further be covered with one or more over-coating layer(s). The over-coating layer(s) can be applied to the enteric coating layered pellets by coating or layering procedures in suitable equipments such as coating pan, coating granulator or in a fluidized bed apparatus using water and/or organic solvents for the layering process.

Final Dosage Form

The prepared pellets may be filled in hard gelatine capsules or compressed with suitable tablet excipients into a tableted multiple unit formulation. Final dosage forms include effervescent tablets, and also combinations of omeprazole with other active ingredients, such as for instance antibacterial substances, NSAID(s), motility agents or antacids.

Experimental Section

Examples 1 and 2: Test of omeprazole pellets layered with two different types of low viscosity HPMC used as a constituent of the separation layer.

Omeprazole pellets prepared according to the description in EP 247 983 (correspond to pellets from a Losec® capsule) were tested with respect to rate of release of omeprazole. According to the marketing approval for the Losec® capsule formulation at least 75% of the omeprazole in a dose must be released within 30 minutes in a buffer solution.

The pellets were pre-exposed to simulated gastric fluid USP (without enzyme) at 37° C. for 2 hours. Thereafter the drug release in buffer solution pH 6.8 at 30 minutes was determined by liquid chromatography. The buffer solution pH 6.8 was a mixture of 100.0 parts of simulated gastric fluid USP (without enzyme) and 80.0 parts of 0.235 M disodium hydrogen phosphate solution, pH should be between 6.75 and 6.85. The simulated gastric fluid USP (without enzyme) was prepared by dissolving 2.0 g NaCl and 7.0 ml conc. HCl and add water to 1000 ml. The 0.235 M disodium hydrogen phosphate solution was prepared by dissolving 41.8 g $Na_2HPO_4 \cdot 2H_2O$ and add water to 1000 ml.

The composition of the tested omeprazole pellets was as follows.

I. Core material with the following composition was prepared.

| Core material | |
| --- | --- |
| Omeprazole | 10.4 kg |
| Mannitol | 74.3 kg |
| Hydroxypropylcellulose | 3.1 kg |
| Microcrystalline cellulose | 2.1 kg |
| Lactose anhydrous | 4.2 kg |
| Disodium hydrogen phosphate | 0.41 kg |
| Sodium lauryl sulphate | 0.26 kg |
| Water approx | 19 kg |

II. The prepared core material was coating layered with a separating layer consisting of HPMC, type A or type B. The separating layers with the following composition were applied in the stated amount.

| Separating layer | |
| --- | --- |
| Uncoated pellets from above | 120 kg |
| Hydroxypropyl methylcellulose 6cps | 4.8 kg |
| Water | 96 kg |

III. The prepared core material with a separating layer was further coating layered with an enteric coating of the following composition.

| Enteric coating layer | |
|---|---|
| Prepared pellets from above | 120 kg |
| Methacrylic acid copolyme | 27.3 kg |
| Polyethylene glycol | 2.7 kg |
| Water | 150 kg |

Omeprazole pellets prepared with separating layer of two different qualities of HPMC 6 cps, i.e type A and type B, were tested according to the description above. The pellets were prepared from the same batch of omeprazole, and with the same enteric coating material. The release of omeprazole within 30 minutes in a buffer solution was determined.

Cloud point determination was performed with two different apparatuses. In Example 1 a commercial equipment from Mettlers was used and in Example 2 a spectrophotometer equipped with a heating coil and stirring function was used. The experimental conditions and used apparatuses are described below.

| Pellets containing HPMC | Cloud point [° C.] Ex. 1 (n=2) | Cloud point [° C.] Ex. 2 (n=1) | Release of omeprazole from enteric coated pellets [%] |
|---|---|---|---|
| Type A | 44.4 | 42.5 | 69 (60–84) |
| Type B | 47.5 | 47.2 | 93 (93–94) |

Figure 2:
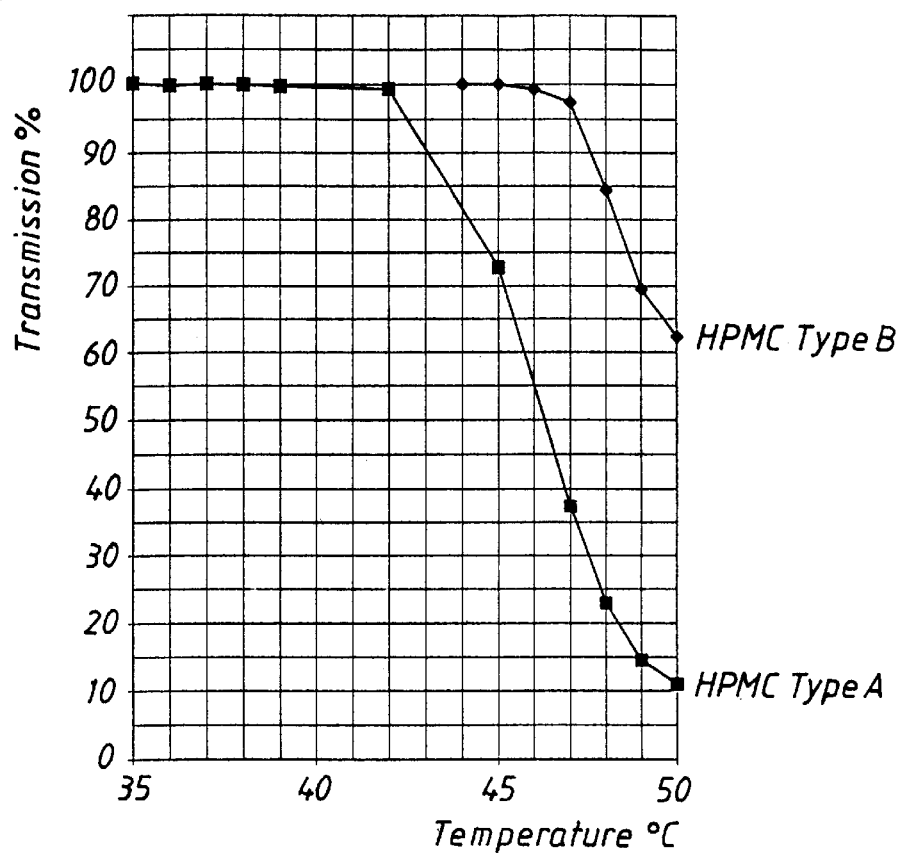
FIG. 2 shows the same experiment as FIG. 1 described in Example 2 below, but the cloud point determination has been performed in another equipment.

The results from cloud point determination for the two HPMC qualities are shown in FIGS. 1 and 2. As can be seen in the table above with the HPMC Type A the release of omeprazole was not acceptable for a pharmaceutical product, but with the HPMC Type B none of the discussed problems with the rate of release of omeprazole in an oral formulation occured.

Results from a number of experiments with different batches of HPMC indicate that HPMC with a cloud point of at least 45.6° C. is desirable in fulfilling the regulatory requirements on rate of release of omeprazole, when the cloud point determination is performed in a commercial Mettler instrument.

Cloud point determination of the HPMC types in the Mettler instrument was conducted in the following way. The cloud point of the HPMC types was determined in a mixed solution of phosphate buffer 0.235 M and simulated gastric fluid pH 1.2 in the proportions 4:5. The mixed solution had a pH of 6.75–6.85. The concentration of HPMC 6 cps in the mixed solution was 1.2% (w/w). It is essential for the specificity of the cloud point determination that this system is used in the choosen instrument. The Mettler instrument comprises the following parts: Mettler FP90 Central processor, FP81C Measuring unit and ME-18572 boiling point tubes. A temperature range of 35.0 to 55.0° C. was used and a heating rate of 1.0° C./min. The results are shown in FIG. 1.

Alternatively, a spectrophotometer equipped with a heating coil and a stirring function was used for the cloud point determination. The concentration of HPMC in the buffer solution was 1.0% (w/w). The equipment measured corresponding temperature and transmission values. Depending on the character of the HPMC to be analysed, the temperature interval of interest varies. A temperature range of 35–50° C. was relevant for most samples. A delay time of 5 minutes at each new temperature setting was used before transmission reading. The results are shown in FIG. 2.

Example 3: Test of different types of low viscosity HPMC used as binding agent in the preparation of core material for pellets.

I. Core material with the following composition was prepared by spray layering in a fluidized bed. An aqueous suspension of omeprazole magnesium salt and HPMC was sprayed onto sugar spheres. Two batches of pellets were prepared using HPMC type A and type B, respectively. The same batch of omeprazole-Mg was used for both experiments.

| Sugar spheres | 200 g |
|---|---|
| Omeprazole-Mg | 200 g |
| Hydroxypropyl methylcellulose 6 cps | 30 g |
| Water | 920 g |

Figure 3:
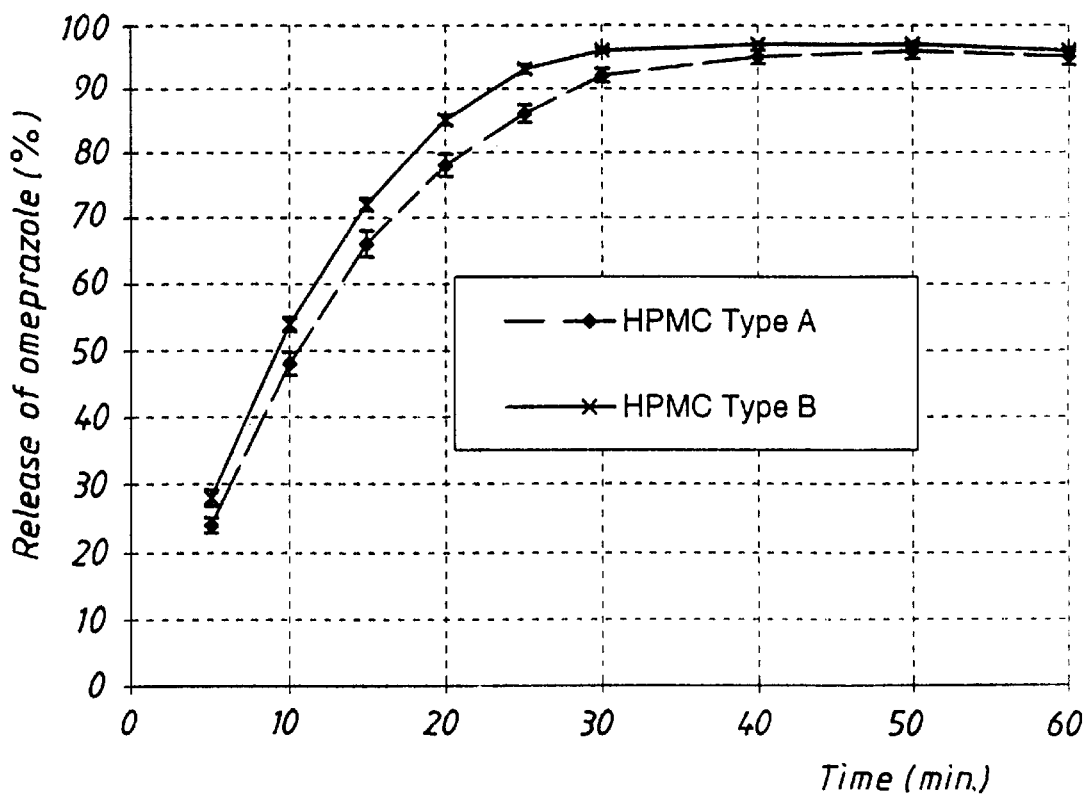
FIG. 3 shows two graphs representing the release of omeprazole from core material with two different batches of low viscosity HPMC used as binding agent described in Example 3 below. The bars represent standard error of the mean. The release of omeprazole was followed by spectrophotometric determinations at 302 nm, and the graphs show that the release of omeprazole was delayed with a binding agent of the HPMC Type A compared with Type B.

The prepared pellets were tested with respect to rate of release of omeprazole in buffer solution pH 6.8 with identical composition as in Example 1, 37° C., paddle speed 100 rpm. The release of omeprazole was followed by spectrophotometric determination (302 nm) and the results are presented in FIG. 3. The graphs show that the release of omeprazole was delayed for the HPMC Type A compared with Type B. Since the pellets were not coated with a separating layer and an enteric coating layer they were not pre-exposed to simulated gastric fluid.

What is claimed is:

1. An enteric coated oral formulation comprising:
   (a) a core material which comprises an active ingredient selected from the group consisting of omeprazole, an alkaline salt of omeprazole, the (–)-enantiomer of omeprazole and an alkaline salt of the (–)-enantiomer, and, optionally, a binding agent in admixture with the active ingredient;
   (b) a separating layer; and
   (c) an enteric coating layer,
   wherein one or more formulation constituents selected form the group consisting of the binding agent and the separating layer comprise a hydroxypropyl methylcellulose (HPMC) of low viscosity with a cloud point of at least 45.6° C., and
   wherein the light transmission at cloud point of a system comprising the HPMC dissolved in a concentration of 1.2% (w/w) in a mixed solution of phosphate buffer 0.235M and simulated gastric fluids pH 1.2 in the proportions 4:5 at a pH of 6.75–85 is 96%.

2. An enteric coated oral formulation comprising:
   (a) a core material which comprises an active ingredient selected from the group consisting of omeprazole, an alkaline salt of omeprazole, the (–)-enantiomer of omeprazole and an alkaline salt of the(–)-enantiomer, and an optional binding agent in admixture with the active ingredient;
   (b) a separating layer; and
   (c) an enteric coating layer,
   wherein one or more formulation constituents selected form the group consisting of the binding agent and the separating layer comprise a hydroxypropyl methylcellulose (HPMC) of low viscosity with a cloud point of at least 44.5° C., and
   wherein the light transmission at cloud point of a system comprising the HPMC dissolved in a concentration of 1.0% (w/w) in a mixed solution of phosphate buffer 0.235M and simulated gastric fluids pH 1.2 in the proportions 4:5 at a pH of 6.75–85 is 95%.

3. The formulation according to claim 1 or 2, wherein the core material further comprises an alkaline reacting compound.

4. The formulation according to claim 1 or 2, wherein the active ingredient is additionally in admixture with a pharmaceutically acceptable excipient selected from the group consisting of surfactants, fillers, disintegrating agents, alkaline additives and mixtures thereof.

5. A process for the manufacture of the enteric coated oral pharmaceutical formulation according to claim 1 or 2, comprising the steps:

(a) forming the core material comprising the active ingredient and optional binding agent;

(b) applying the separating layer onto the core; and (c) applying the enteric coating layer onto the core coated with the separating layer, wherein one or more formulation constituents selected form the group consisting of the binding agent and the separating layer comprise the HPMC of low viscosity.

6. The process according to claim 5, wherein an alkaline reacting compound is mixed with the active ingredient and optional binding agent to form the core material.

7. The method according to claim 2, wherein the separating layer comprises the HPMC of low viscosity.

8. The method according to claim 2, wherein the enteric coating layer comprises a methacrylic acid copolymer.

9. The method according to claim 2, wherein the binding agent is a HPMC of low viscosity.

10. The method according to claim 2, wherein the HPMC of low viscosity has a viscosity of less than 7.2 cps in 2% aqueous solution.

11. The method according to claim 2, wherein the active ingredient is omeprazole.

12. The method according to claim 2, wherein the active ingredient is a magnesium salt of omeprazole.

13. The method according to claim 2, wherein the active ingredient is a magnesium salt of the (−)-enantiomer of omeprazole.

14. The formulation according to claim 1 or 2, wherein the separating layer comprises the HPMC of low viscosity.

15. The formulation according to claim 14, wherein the enteric coating layer comprises a methacrylic acid copolymer.

16. The formulation according to claim 1 or 2, wherein the binding agent is a HPMC of low viscosity.

17. The formulation according to claim 1 or 2, wherein the HPMC of low viscosity has a viscosity of less than 7.2 cps in 2% aqueous solution.

18. The formulation according to claim 1 or 2, wherein the active ingredient is omeprazole.

19. The formulation according to claim 1 or 2, wherein the active ingredient is a magnesium salt of omeprazole.

20. The formulation according to claim 1 or 2, wherein the active ingredient is a magnesium salt of the (−)-enantiomer of omeprazole.

21. A method for the treatment of gastrointestinal diseases in mammals comprising administering to a host in need thereof a therapeutically effective amount of the pharmaceutical formulation according to any one of claims 1 or 2.

* * * * *

UNITED STATES PATENT AND TRADEMARK OFFICE
CERTIFICATE OF CORRECTION

PATENT NO. : 6,090,827
DATED : July 18, 2000
INVENTOR(S) : Erickson et al.

It is certified that error appears in the above-identified patent and that said Letters Patent is hereby corrected as shown below:

Column 8, claim 1,
Line 46, delete "6.75-85" and insert therefor -- 6.75-6.85 --.

Claim 2,
Line 66, delete "6.75-85" and insert therefor -- 6.75-6.85 --.

Claim 7-13,
Delete "claim 2" and insert therefor -- claim 21 --.

Signed and Sealed this

Eleventh Day of December, 2001

Attest:

NICHOLAS P. GODICI
Acting Director of the United States Patent and Trademark Office Attesting Officer